United States Patent
Heavens et al.

(10) Patent No.: US 7,412,760 B2
(45) Date of Patent: Aug. 19, 2008

(54) CRACK TEST FOR STAMPED FLANGE

(75) Inventors: Glenn G. Heavens, Cheshire, CT (US);
Brian Putetti, Wolcott, CT (US)

(73) Assignee: Illinois Tool Works Inc., Glenview, IL (US)

(*) Notice: Subject to any disclaimer, the term of this patent is extended or adjusted under 35 U.S.C. 154(b) by 503 days.

(21) Appl. No.: 11/228,154

(22) Filed: Sep. 16, 2005

(65) Prior Publication Data
US 2007/0062298 A1   Mar. 22, 2007

(51) Int. Cl.
*G01M 19/00* (2006.01)
(52) U.S. Cl. ............ 29/407.01; 73/865.9; 83/102
(58) Field of Classification Search ............ 29/407.01; 73/865.9; 83/102
See application file for complete search history.

(56) References Cited

U.S. PATENT DOCUMENTS 7,117,574 B2 * 10/2006 Liu et al. .............. 29/407.01
7,162,799 B2 * 1/2007 Moore et al. .......... 29/407.01 X

* cited by examiner

*Primary Examiner*—Thomas P Noland
(74) *Attorney, Agent, or Firm*—Mark W. Croll; Paul F. Donovan

(57) ABSTRACT

A punch is provided with a detection system for evaluating crack defects in waste material removed during a clipping operation. The punch includes a clip ring and a clip insert for shearing excess material from a part processed therein. The excess material is engaged around the clip ring when sheared from the part. Frictional resistance between the waste material and the clip ring is evaluated in determining potential crack defects in the waste material.

20 Claims, 4 Drawing Sheets

CRACK TEST FOR STAMPED FLANGE

FIELD OF THE INVENTION

The present invention relates generally to parts and pieces made by stampings and/or progressive stampings; and, more particularly, the invention relates to devices and procedures for testing the integrity of stamped flanges.

BACKGROUND OF THE INVENTION

Parts and pieces of many different types and shapes are made by stampings and progressive stampings for use in a variety of different assemblies and constructions. Metal can be shaped into many different forms and configurations by the application of force causing a metal blank to conform to the shape of a die used while applying the force. Simple parts and pieces can sometimes be made by a single stamping. In a single stamping, force is applied in a single event so that the metal conforms to a die used while applying the force. For more complex parts or parts taking a shape quite different from the original metal blank, progressive stampings are used. In progressive stampings, a series of dies are used in a series of stamping events, with each die and each stamping event forming the metal in stages from the original blank to the desired final formation.

The loads applied to the metal in a stamping process can cause a variety of flaws to form in stamped metal pieces and parts. For example, the metal may not conform as desired to the die used in the stamping process. Further, the force applied can cause cracks and other flaws in the metal. It is necessary to remove defective parts so that the defective parts are not incorporated into a final assembly. While visual inspection can be used for some defects, visual inspection by individuals is slow and not completely reliable if the defects are small.

Stamping is often used to make parts and pieces inexpensively, since a stamping event is a rapid occurrence. Accordingly, parts can be formed quickly and inexpensively, with minimal waste. To ensure a high percentage of quality parts are shipped to customers cost effectively, testing procedures for stamped parts must be performed rapidly and reliably. Preferably, a testing method occurs as quickly as the stamping process so that testing or inspection does not slow the overall process of making the part.

It is known to use stamping techniques to form a variety of parts having a head or a flange at an end thereof. For example, a substantially cylindrical or tubular part can be stamped to have a peripheral flange at one end. The stamping process may include a first formation process to form the flange in a gross, oversize configuration. A more precise clipping process is then used to ensure a reliable diameter by shearing away any excess material in the preformed flange. In a clipping process a peripheral portion of the stamped flange is removed as an annular ring so that the remaining portion on the part is of the desired diameter, and is positioned properly in the part.

A process to form a flange as described above can cause cracks to occur in the flange portion of the part. Cracks can cause the part to seal inadequately causing leaks, or to support inadequately and cause failure. Further, cracks can migrate over time, causing the part to fail prematurely. Accordingly, it is desirable to identify parts in which even small cracks have occurred before the part is put into use and fails. While complex, detailed metal analysis could be performed on each part, such testing is cost prohibitive for many parts that must be supplied inexpensively.

Accordingly, it is desirable to provide a device and process for testing stamped flange parts to reliably identify parts in which cracks have been created during the formation process.

SUMMARY OF THE INVENTION

The present invention provides a process and apparatus for determining if cracks have occurred in a stamped, clipped flange by testing the annular ring of waste material removed during the clipping step.

In one aspect thereof, the present invention provides a process to evaluate a part with steps of preforming the part, clipping the preformed part to generate a finished part and a waste piece, evaluating the waste piece for the presence of crack defects; and rejecting the finished part when the waste part exhibits crack defects.

In another aspect thereof, the present invention provides a process for forming a head on a part and evaluating the head for crack defects. The process has steps of pre-forming the head on the part, clipping a peripheral portion of the head to provide a finished head while generating a generally annular waste piece, providing the waste piece about a body; sliding the waste piece from the body; evaluating the frictional resistance between the waste piece and the body; and rejecting the part with the finished head if the frictional resistance between the annular waste piece and the body is less than a pre-established threshold.

In a still further aspect thereof, the present invention provides a clipping assembly with a die block supporting a clip insert and a punch assembly including an axially translatable plunger having a clip ring receivable in the clip insert for shearing material between the clip ring and the clip insert. A floating punch has an end in the plunger and is biased in the plunger away from the clip insert. A proximity detector determines a position of the end. A grasping means captures waste material on the clip ring as the plunger is moved away from the clip insert.

An advantage of the present invention is providing an apparatus and process for reliably determining the possible presence of cracks in an annular flange formed by stamping or progressive stamping processes.

Another advantage of the present invention is providing a crack detection process which operates quickly in conjunction with a stamping process used to form a part so that testing is performed quickly and reliably without slowing the stamping process.

Another advantage of the present invention is providing a crack detection process for stamped flanges which does not add significant cost to the manufacturing process to make the stamped part.

Other features and advantages of the invention will become apparent to those skilled in the art upon review of the following detailed description, claims and drawings in which like numerals are used to designate like features.

Figure 1:
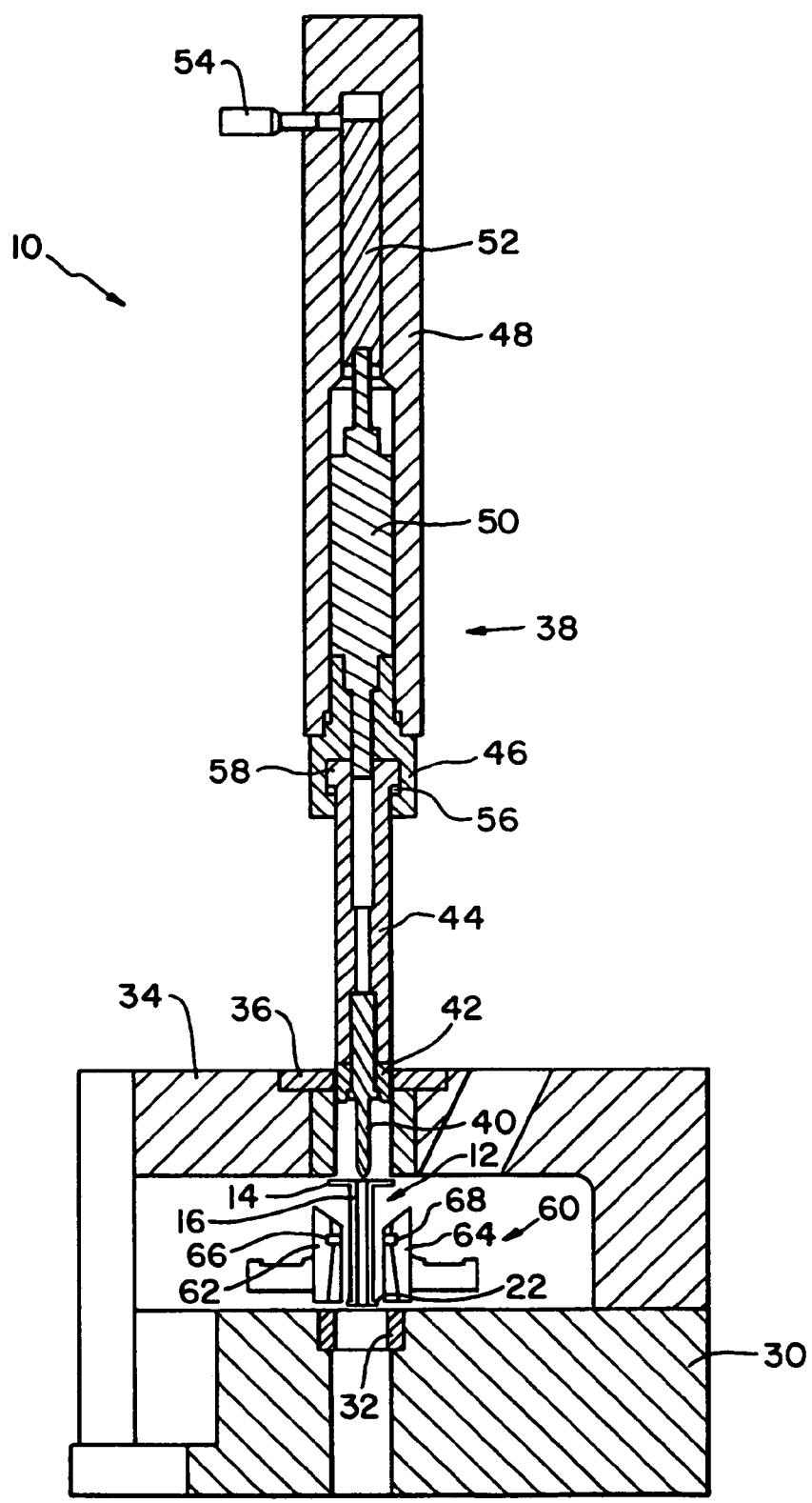
FIG. 1 is a cross-sectional view of a press prepared to clip a flange on a part, all in accordance with the present invention.

Before the embodiments of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein are for the purpose of description and should not be regarded as limiting. The use herein of "including", "comprising" and variations thereof is meant to encompass the items listed thereafter and equivalents thereof, as well as additional items and equivalents thereof.

DETAILED DESCRIPTION OF THE PREFERRED EMBODIMENT

Referring now more specifically to the drawings and to FIG. 1 in particular, a punch press 10 in accordance with the present invention is shown. Press 10 is configured for processing a part 12 in clipping and crack detection processes also in accordance with the present invention. Press 10 is configured to clip a peripheral edge of a preformed head or flange 14 on part 12.

Part 12 includes a tubular shank 16 from which preformed flange 14, at one end thereof, may have been formed in a previous stamping process, prior to processing in press 10. Punch press 10 is configured and operated to clip a peripheral annular ring waste segment 18 from preformed flange 14 to thereby form a finished flange 20 (FIGS. 2 & 3) from preformed flange 14. Accordingly, finished flange 20 has a precise diameter and is positioned accurately, which may be difficult to achieve the initial stamping of preformed head or flange 14.

In the exemplary embodiment, part 12 further includes an end flange 22 opposite preformed flange 14. However, it should be understood that the present invention can be used for stamping processes forming other types of parts than part 12 shown. The exemplary embodiment having a relatively long shank with flanges on both ends is merely exemplary. For example, as those skilled in the art will understand readily from the following description, the present invention can be used also when forming flanges on parts of other shapes or when forming other parts, perhaps even flat parts, having a clipping process in which a continuous annular waste piece is generated. For example, the present invention can be used if head or flange 14 is an outwardly extending head of a part having a solid shank.

Punch press 10 includes a die block 30 having a clip insert 32 therein. Die block 30 supports a guide block 34 having a guide ring 36. A punch assembly 38 is configured and arranged for operating together with guide block 30 and the equipment supported thereby for clipping the peripheral edge from preformed flange 14. Accordingly, punch assembly 38 is in axially translatable toward and away from clip insert 32 through guide block 34 and guide ring 36 therein.

Figure 2:
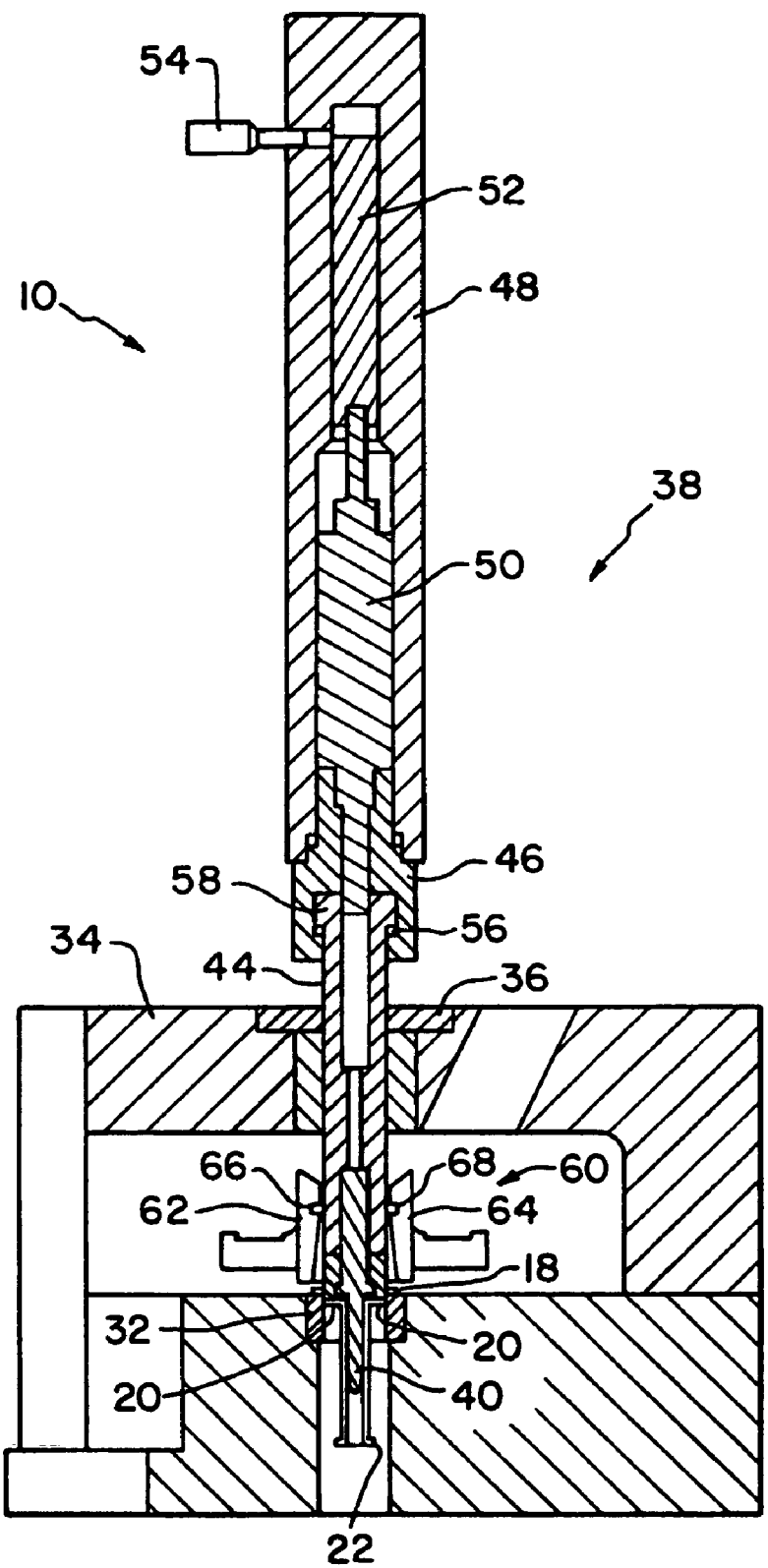
FIG. 2 is a cross-sectional view similar to that of FIG. 1, but illustrating the press and part as crack testing begins after the clipping step has been completed.
Figure 3:
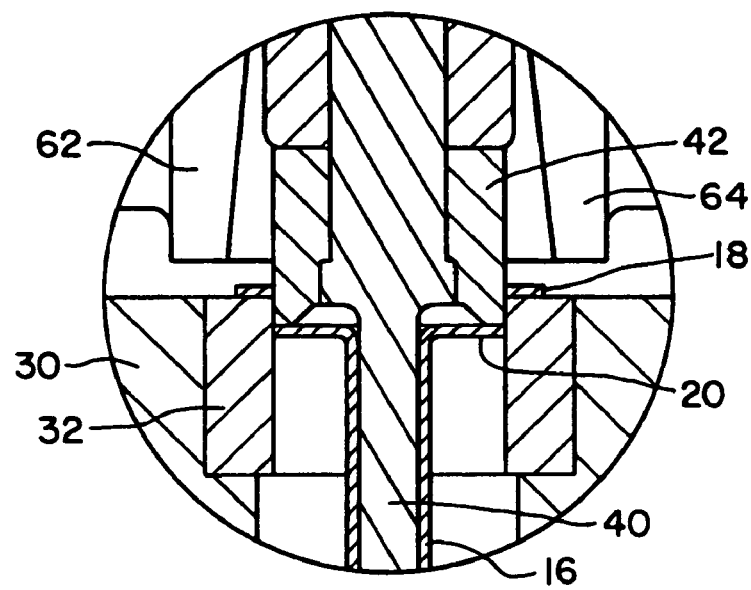
FIG. 3 is an enlarged fragmentary cross-sectional view of a portion of the press shown in FIG. 2.

Punch assembly 38 includes a pilot 40 which is inserted into shank 16 for centering part 12 relative to press 10, as can be seen most clearly in FIG. 2. A clip ring 42 is forced against preformed flange 14, and in cooperation with clip insert 32 cuts the peripheral waste ring 18 from preformed flange 14, thereby forming finished flange 20.

Pilot 40 and clip ring 42 are held in a floating punch 44 retained by a punch chuck 46 in a plunger 48. A cylinder 50 in plunger 48 applies a continuous force pulling floating punch 44 into punch chuck 46. A steel rod 52 extends from cylinder 50 toward a proximity switch 54 configured to detect the presence of steel rod 52 within a prescribed axial range.

Punch chuck 46 defines a cavity 56 receiving a head 58 of floating punch 44, and provides axial space as shown whereby head 58 can move relative to punch chuck 46.

Figure 5:
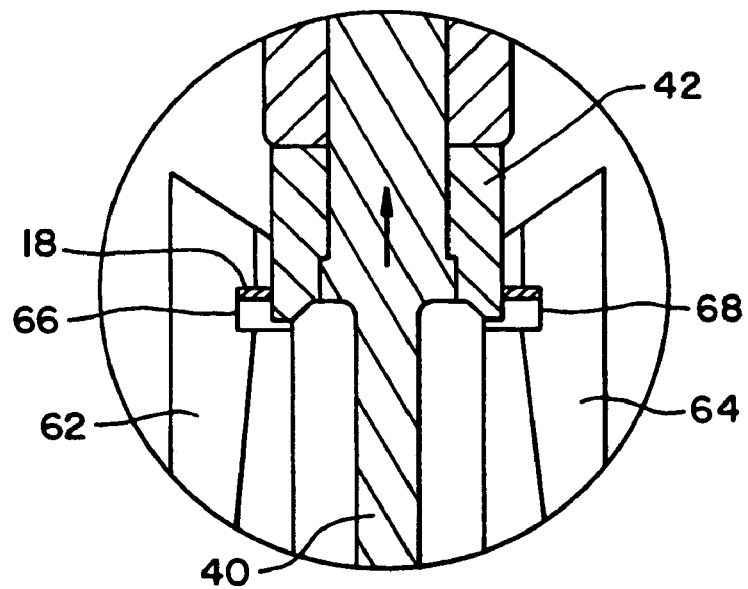
FIG. 5 is an enlarged fragmentary cross-sectional view of a portion of the press as shown in FIG. 4.
Figure 4:
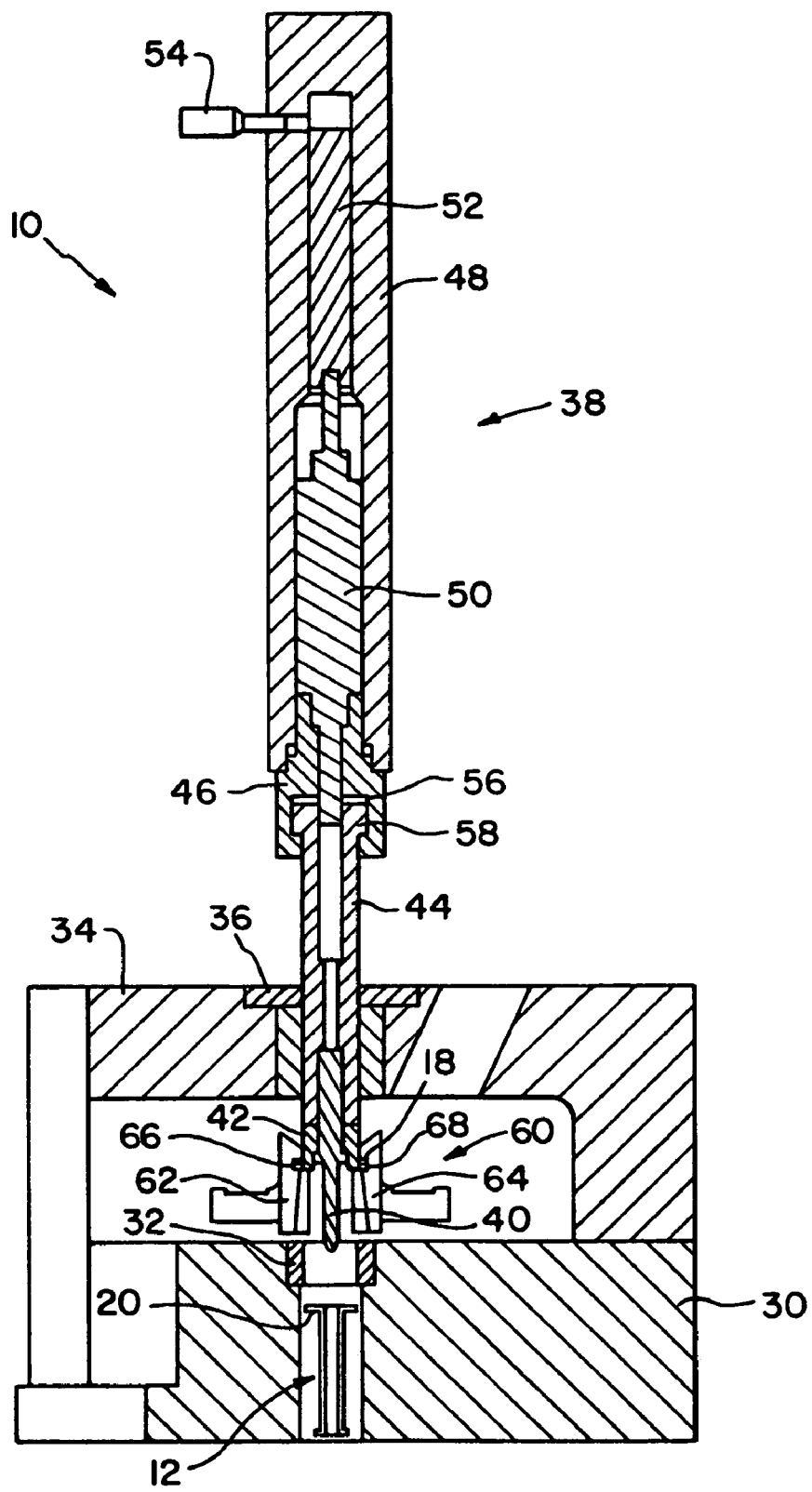
FIG. 4 is a cross-sectional view similar to FIGS. 1 and 2, but illustrating the press in a later stage of the process, when the integrity test of the present invention is being performed.

A waste ring removal assembly 60 is provided for removing waste ring 18 from clip ring 42 as punch assembly 38 is retracted. Transfer fingers 62, 64 include notches 66, 68 for grasping waste ring 18, stripping it from clip ring 42 and transferring waste ring 18 to scrap processing. As shown in FIGS. 4 and 5, waste ring 18 is caught in notches 66, 68 for stripping from clip ring 42 as punch assembly 38 is retracted.

Part 12 is formed by a stamping or the like, with a gross formation of preformed flange 14. During the formation of preformed flange 14, or during the subsequent clipping operation performed by press 10 to separate waste ring 18 from finished flange 20 cracks may form in preformed flange 14. In most circumstances, annular waste ring 18 will exhibit cracks if cracks are present in the region of finished flange 20. Accordingly, detecting defects or flaws such as cracks in waste ring 18 indicates that similar cracks or flaws may exist in finished flange 20. Similarly, if waste ring 18 exhibits no cracks or flaws it is very unlikely that any crack or flaw will exist in finished flange 20. Accordingly, the present invention takes advantage of the ability to evaluate a condition of waste ring 18 to determine the possibility of defects in finished flange 20. Although an occasional part 12 having an acceptable finished flange 20 may be rejected because of cracks found only in waste ring 18, such occurrences are unlikely and rare and the occasional waste therefrom is acceptable.

FIG. 1 illustrates punch press 10 and part 12 prior to commencement of a flange clipping operation. Part 12 is positioned to start the clipping process, and punch assembly 38 is retracted.

In FIG. 2, part 12 is guided through clip insert 32 as any excess material of preformed flange 14 is sheared away as waste ring 18, to size and position finished flange 20 properly and accurately. Waste ring 18 remains positioned about clip ring 42 from the clipping process. As shown in FIG. 4, finished part 12 falls from die block 30 as the press returns to its starting position.

When waste ring 18 is continuous, solid and intact without cracks, waste ring 18 is engaged around clip ring 42 with some frictional resistance. Resistance to the upward movement of floating punch 44 is created as transfer fingers 62, 64 hold waste ring 18. The resistance is in the opposite direction of the normal biasing force exerted by cylinder 50. The frictional resistance overcomes the biasing force supplied by cylinder 50 and thereby causes a brief displacement of floating punch 44 relative to plunger 48 during the return step. For a brief time, floating punch 44 remains in a substantially fixed position while plunger 48 continues along its path of retraction and punch chuck 46 moves relative to head 56 as permitted by the size of cavity 56. Rod 52 also remains substantially fixed as plunger 48 moves, causing a relative axial displacement between the end of rod 52 and proximity switch 54. Proximity switch 54 detects an absence of steel rod 52 and allows press 10 to continue the return stroke. The relative displacement between floating punch 44 and plunger 48 is limited by the difference in axial lengths of head 58 and cavity 56, so that at some point in the return stroke of punch assembly 38 the frictional resistance of waste ring 18 on clip ring 42 is overcome, stripping waste ring 18 from clip ring 42. The momentary absence of steel rod 52 from detection by proximity switch 54 is an indication that waste ring 18 is solid and intact, in the that it provided a predetermined frictional resistance to movement on clip ring 42 sufficient to overcome the biasing force of cylinder 50. This interpretation is extrapolated to the condition of finished flange 20, and part 12 is determined to be acceptable.

If preformed flange 14 includes cracks or similar defects, or if cracks are created during the clipping process described the defects extend into waste ring 18. As a result, waste ring 18 will fit more loosely around clip ring 42 than if waste ring 18 is without defects. As plunger 48 is returned to the start position, the frictional resistance of waste ring 18 on clip ring 42 is insufficient to overcome the biasing force of cylinder 50. Accordingly, in this condition, no relative movement occurs between floating punch 44 and plunger 48. Proximity switch 54 fails to detect an absence of steel rod 52, and a signal is sent to terminate operation of punch press 10. A light or other indicator can be used to alert an operator that part 12 may contain a defect, and/or press 10 can be shut down. Part 12 can be removed from the stream of parts being produced or part 12 can be flagged for later removal as normal operation of press 10 continues.

Defect detection in waste ring 18 is performed as part of the routine stroke of punch press 10. Accordingly, evaluation of part 12 is performed immediately as finished flange 20 is formed, and no delay occurs. No additional time is required to complete the testing or evaluation since the evaluation occurs during a normal return stroke of punch press 10.

Variations and modifications of the foregoing are within the scope of the present invention. It is understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention. The claims are to be construed to include alternative embodiments to the extent permitted by the prior art.

Various features of the invention are set forth in the following claims.

What is claimed is:

1. A process to evaluate a part, comprising:
   preforming the part;
   clipping the preformed part to generate a finished part and a waste piece;
   evaluating the waste piece for the presence of crack defects; and
   rejecting the finished part when the waste part exhibits crack defects.

2. The process of claim 1, including clipping an annular ring as the waste piece.

3. The process of claim 2, said step of evaluating the waste piece including providing the annular ring engaged about a body inserted therein, and evaluating a frictional resistance between the annular ring and the body.

4. The process of claim 3, including engaging the annular waste piece around the body simultaneously with said step of clipping the preformed part.

5. The process of claim 3, including providing the body as a floating component, biasing the component in a first direction with an established force and comparing the frictional resistance as an opposing force to the established force.

6. The process of claim 5, including engaging the annular waste piece around the body simultaneously with said step of clipping the preformed part.

7. The process of claim 1, including providing a clipping assembly comprising:
   a die block supporting a clip insert;
   a punch assembly including an axially translatable plunger and a floating punch having a clip ring receivable in said clip insert for shearing material between said clip ring and said clip insert, said floating punch having an end moveable in said plunger and being biased in said plunger away from said clip insert;
   a proximity detector for determining a position of said end; and
   grasping means for capturing waste material on said clip ring as said plunger is moved away from said clip insert.

8. The clipping assembly of claim 7, said proximity detector being disposed in said plunger.

9. The clipping assembly of claim 7, said grasping means including at least first and second opposed fingers.

10. The clipping assembly of claim 9, said proximity detector being disposed in said plunger.

11. The clipping assembly of claim 10, including a cylinder in said plunger biasing said floating punch.

12. The clipping assembly of claim 7, including a cylinder in said plunger biasing said floating punch.

13. The clipping assembly of claim 12, said proximity detector being disposed in said plunger.

14. The clipping assembly of claim 12, said grasping means including at least first and second opposed fingers.

15. A process for forming a head on a part and evaluating the head for crack defects, said process comprising steps of:
   pre-forming the head on the part;
   clipping a peripheral portion of the head to provide a finished head while generating a generally annular waste piece;
   providing the waste piece engaged around a body;
   sliding the waste piece from the body;
   evaluating the frictional resistance between the waste piece and the body; and
   rejecting the part with the finished head if the frictional resistance between the annular waste piece and the body is less than a pre-established threshold.

16. The process of claim 15, including clipping the head with a punch creating the annular waste piece, and engaging the waste piece around a part of the punch while creating the waste piece.

17. The process of claim 16, including grasping the waste piece while extracting the part of the punch from the waste piece, and evaluating the frictional resistance between the part of the punch and the waste piece as the part of the punch is extracted.

18. The process of claim 16, including providing the part of the punch as a floating component, biasing the floating component in a first direction with an established force and comparing the frictional resistance as an opposing force to the established force.

19. The process of claim 18, including grasping the waste piece while extracting the part of the punch from the waste piece, and evaluating the frictional resistance between the part of the punch and the waste piece as the part of the punch is extracted.

20. The process of claim 15, including providing a clip ring on a floating punch in an axially movable punch assembly for performing said clipping step, biasing the floating punch with an established force in a direction for retracting the punch away from the part, and rejecting the part if the frictional resistance between the waste piece and the clip ring is insufficient to overcome the biasing force.

* * * * *